US006340478B1

(12) United States Patent
Blatt et al.

(10) Patent No.: US 6,340,478 B1
(45) Date of Patent: Jan. 22, 2002

(54) MICROENCAPSULATED AND CONTROLLED-RELEASE HERBAL FORMULATIONS

(75) Inventors: Yoav Blatt; Eugene Kimmelman, both of Rehovot; David Cohen, Petach Tikva; Avner Rotman, Rehovot, all of (IL)

(73) Assignee: Bio Dar Ltd., Yavne (IL)

( * ) Notice: Subject to any disclaimer, the term of this patent is extended or adjusted under 35 U.S.C. 154(b) by 0 days.

(21) Appl. No.: 09/327,752

(22) Filed: Jun. 7, 1999

(51) Int. Cl.[7] .......................... A61K 35/78; A61K 9/14; A61K 9/16; A61K 9/48; A61K 9/20
(52) U.S. Cl. ....................... 424/489; 424/490; 424/451; 424/464; 424/195.1
(58) Field of Search .............................. 424/195.1, 451, 424/464, 490, 489

(56) References Cited

U.S. PATENT DOCUMENTS 4,708,874 A  * 11/1987  De Haan et al.
5,560,928 A  * 10/1996  Defelice
5,780,060 A     7/1998  Levy er al. .................. 424/489
5,985,282 A  * 11/1999  Haveson

FOREIGN PATENT DOCUMENTS

EP            0 702 957        3/1998        .......... A61K/35/78

* cited by examiner

Primary Examiner—Thurman K. Page
Assistant Examiner—Amy E Pulliam
(74) Attorney, Agent, or Firm—Abelman, Frayne & Schwab

(57) ABSTRACT

There is provided an orally-administrable formulation for the controlled release or stable storage of a granulated herb, comprising a granulated herb and at least one carrier, adjuvant or excipient therefor. Preferably, the formulation is characterized in that the total in vitro dissolution time of said formulation required for release of 75% of the active ingredients available from the formulation is between about 4 and about 18 hours, as determined by the U.S.P. XXIII paddle method at a paddle speed of 150 rpm, using simulated intestinal fluid without the digestive enzymes normally found in intestinal fluid, containing 0.1% w/w sodium dodecyl sulfate (SDS), at pH 6.8, and a temperature of 37° C. A process for the preparation of such formulation is also provided.

15 Claims, 8 Drawing Sheets

US 6,340,478 B1

MICROENCAPSULATED AND CONTROLLED-RELEASE HERBAL FORMULATIONS

FIELD OF THE INVENTION

Figure 1:
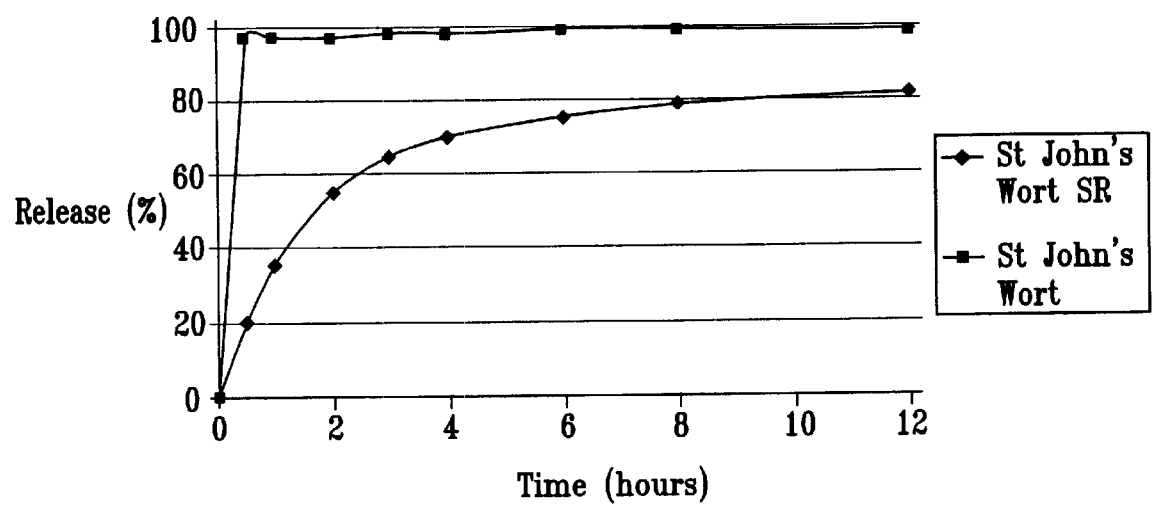

The present invention relates to formulations for the controlled or extended release of certain bioactive compounds, and to processes for the preparation of the same.

BACKGROUND OF THE INVENTION

Powdered and granulated herbal (botanical) extracts and dried, ground dry plants are good and well accepted sources of certain bioactive compounds.

Thus, for example, garlic is a good source for Allicin and γglutamyl peptides; St. John's Wort is a source for Hypericin and Hyperforine, and Echinacea is a source for certain Echinosides.

It has been established that many botanical and herbal extracts and plants can serve as an important nutritional supplement and therapeutic materials. However, it has been found that many of these materials are unstable and when stored for long periods, the active ingredients are often eliminated or otherwise rendered inactive.

SUMMARY OF THE INVENTION

The present invention seeks to provide improved herbal preparations which preparations offer a convenient oral dosage form of herbs for supplying optimum plasma concentrations of the biologically active compounds contained in the herbs (such as Ginsenoside Rγ1 and Ginsenoside Rβ1 from extracts of Panax Ginseng) and which facilitates user compliance with recommended procedures.

There is thus provided in accordance with a preferred embodiment of the invention an orally-administrable formulation for the controlled release of a ground herb, said formulation comprising ground herb and at least one carrier, adjuvant or excipient therefor.

There is also provided in accordance with a preferred embodiment of the invention an orally-administrable formulation for the stable storage of a ground herb, said formulation comprising a ground herb and at least one carrier, adjuvant or excipient therefor.

In the context of the present description and claims, the term "granulated herb" will be understood to refer to both powdered and granulated forms of both herbal extracts and herbal plants or portions of herbal plants, which extracts, plants or portions thereof have been ground to a particle size within the range of about 100 to about 2000 μm diameter, preferably in the range of about 300 to about 1000 μm diameter.

In one preferred embodiment of the invention, the orally-administrable formulation for the controlled release of granulated herb comprises granulated herb and at least one carrier, adjuvant or excipient therefor, and is characterized in that the total in vitro dissolution time of the formulation required for release of 75% of the active ingredient available from the formulation, is between about 4 and about 18 hours, as determined by the U.S.P. XXIII paddle method at a paddle speed of 150 rpm, using simulated intestinal fluid without the digestive enzymes normally found in intestinal fluid, containing 0.1% w/w sodium dodecyl sulfate (SDS), at pH 6.8, and a temperature of 37° C.

In one preferred embodiment of the invention, the formulation is characterized in that it contains from 1 to 95 wt. % granulated herb.

In another preferred embodiment of the invention, the formulation is in a form selected from the group consisting of: a matrix tablet, a multicomponent formulation, a microcapsule of generally spherical shape, a microcapsule of generally non-spherical shape, a capsule containing microcapsules, and a tablet containing microcapsules.

In another preferred embodiment of the invention, the formulation comprises granulated herbs mixed or coated with an adjuvant or mixture of adjuvants selected from the group consisting of synthetic polyvinyl-type polymers, synthetic polyethylene-type polymers, cellulose-type polymers, synthetic polyacrylate-type polymers, fats, waxes, sugars and sugar alcohols.

In one preferred embodiment of the invention, the formulation is in the form of a tablet comprising granulated herbs embedded in a mixture of polyvinyl chloride an polyvinyl acetate, and magnesium stearate as a lubricant.

In another preferred embodiment of the invention, the formulation is in the form of a tablet comprising granulated herb embedded in a mixture of polyvinyl chloride and ethylcellulose, magnesium stearate as lubricant, and a material selected from hydroxypropyl methyl cellulose, sodium carboxymethyl cellulose and paraffin.

In a preferred embodiment of the invention, the formulation is in the form of a hard gelatin two-piece capsule filled with microcapsules containing granulated herb.

In another preferred embodiment of the invention, the formulation is in the form of a tablet comprising microcapsules.

The invention also comprises a process for the preparation of an orally-administrable formulation for the controlled release of a granulated herb, said formulation comprising granulated herb and at least one carrier, adjuvant or excipient therefor, said process comprising the steps of;
  providing a granulated herb; and
  incorporating said granulated herb into said at least one carrier, adjuvant or excipient therefor;
  wherein said formulation is characterized in that the total in vitro dissolution time of said formulation required for release of 75% of the active ingredients from said formulation is between about 4 and about 18 hours, as determined by to the U.S.P. XXIII paddle method, using simulated intestinal fluid without the digestive enzymes normally found in intestinal fluid, containing 0.1% w/w sodium dodecyl sulfate (SDS), at pH 6.8, and temperature of 37° C.

In one preferred embodiment of the invention, the process is characterized in that the granulated herb is (i) mixed or coated with an adjuvant or mixture of adjuvants selected from the group consisting of synthetic polyvinyl-type polymers, synthetic polyethylene-type polymers, cellulose-type polymers, synthetic polyacrylate-type polymers, fats, waxes, sugars and sugar alcohols, and (ii) then compressed into tablets.

In another preferred embodiment of the invention, the process is characterized in that the granulated herb is (i) mixed or coated with an adjuvant or mixture of adjuvants selected from the group consisting of synthetic polyvinyl-type polymers, synthetic polyethylene-type polymers, cellulose-type polymers, synthetic polyacrylate-type polymers, fats, waxes and sugars , (ii) then processed into a form selected from the group of microcapsules and pellets, and (iii) the microcapsules or pellets are filled into hard gelatin capsules.

In a preferred embodiment of the invention, the process is characterized in that the granulated herb is (i) mixed or coated with an adjuvant or mixture of adjuvants selected from the group consisting of synthetic polyvinyl-type polymers, synthetic polyethylene-type polymers, cellulose-type polymers, synthetic polyacrylate-type polymers, fats, waxes and sugars, (ii) then processed into a form selected from the group of microcapsules and pellets, and (iii) said microcapsules or pellets are compressed into tablets.

There is also provided in accordance with a preferred embodiment of the invention an orally-administrable formulation for the controlled release of a granulated herb, comprising particles of granulated herb coated with a film comprising a mixture of at least one water soluble polymer and at least one water insoluble polymer, the at least one water soluble polymer and the at least one water insoluble polymer being present in a ratio that produces a substantially zero order linear release pattern of at least one active ingredient. In one preferred embodiment of the invention, the particles comprise particles which are non-spherically shaped. In another preferred embodiment of the invention, the particles comprise particles which are spherically shaped.

There is also provided in accordance with a preferred embodiment of the invention an orally-administrable formulation for the controlled release of a granulated herb, comprising particles of granulated herb coated with an enteric coating comprising a polymer film comprising a polymer which is insoluble at a pH below about 5.5. In a preferred embodiment of the invention, the particles comprise particles which are non-spherically shaped. In another preferred embodiment of the invention, the particles comprise particles which are spherically shaped.

In a preferred embodiment of the invention, the polymer is soluble at a pH of about 5.5 or higher. In another preferred embodiment of the invention, the polymer is insoluble at a pH below about 5.0.

In one preferred embodiment of the invention, the polymer is hydroxypropylmethyl cellulose phthalate. In another preferred embodiment of the invention, the polymer is cellulose acetate phthalate.

In a preferred embodiment of the invention, the water insoluble polymer is ethyl cellulose.

In another preferred embodiment of the invention, the water soluble polymer is hydroxypropylmethyl cellulose (HPMC).

In a preferred embodiment of the invention, the water insoluble polymer is ethyl cellulose and the water soluble polymer is hydroxypropylmethyl cellulose (HPMC), and the HPMC/ethyl cellulose ratio is substantially from about 0.05 to about 0.40.

In a preferred embodiment of the invention, the content of granulated herb is between about 1 to 95 wt. %.

In accordance with another preferred embodiment of the invention, there is provided a process for producing an orally-administrable formulation for the controlled release of a granulated herb, comprising coating particles of granulated herb with an inner mixed polymer film comprising ethyl cellulose and hydroxypropylmethyl cellulose (HPMC), wherein the HPMC/ethyl cellulose ratio is substantially from about 0 to about 0.40 by weight, and then coating said particles coated with said inner polymer film with an outer polymer film comprising hydroxypropylmethyl cellulose phthalate, wherein the weight ratio of the outer and inner polymer layers is between about 0.2 to 5.

DETAILED DESCRIPTION OF PREFERRED EMBODIMENTS OF THE INVENTION

The oral controlled release dosage formulations of granulated herbs, in accordance with the invention, include matrix formulations, such as matrix tablets, and multiparticulate formulations such as microcapsules.

In one preferred formulation of the invention, non-spherically, irregularly shaped herb granulate particles are coated with a film layer comprising of a water insoluble polymer such as ethyl cellulose and a water soluble polymer such as hydroxypropylmethyl cellulose (HPMC) and plasticizer such as castor oil in an HPMC/ethyl cellulose weight ratio substantially within the range of 0 to 0.4.

The present invention relates to oral controlled and stable release dosage form of granulated herb, especially in either matrix formulations such as matrix tablets or in multiparticulate formulations like microcapsules put into two piece capsules. This is done in order to obtain a drug delivery system of herbal-derived molecules which will ensure a steady supply of the active components for a sustained period. By either embedding the granulated herb into a matrix formulation or incorporating it into a microcapsule formulation, or both, in order to control or extend the release of the components of the herb into the surroundings, the following advantages may be obtained in comparison with conventional release formulations:

A slower in vivo absorption of herbal-derived active molecules, and hence optimal plasma peak values, which thus reduces the occurrence of undesired effects, such as photosensitization caused by high concentrations of hypericin released from St. John's Wort extract.

Prolonged and steady plasma concentrations of herbal-derived active molecules over 12 hours which can help avoid underdosing between dosage intervals.

A significant increase in the relative extent of bioavailability (amount of active ingredient per gram of herb ingested) of herbal-derived active molecules, i.e. the therapeutically relevant component, in comparison to standard release formulations.

Higher tolerability of the active ingredients, i.e., fewer side effects.

Reduction in the number of daily doses required, which together with the higher tolerability can significantly increase user compliance.

Stabilization of the highly sensitive herbal-derived active ingredients and thus extending the shelf life of the product.

Provision of an enteric-coated formulation in those products which are sensitive to the low pH of the stomach and ensuring their release only in the intestine.

Coating and Matrix Materials for Obtaining Controlled Release

Coating and matrix materials which may be used in accordance with the invention are those known in the art for use in controlled-release formulations, such as:

(a) synthetic polymers of the polyvinyl type, e.g. polyvinylchloride, polyvinylacetate and copolymers thereof, polyvinylalcohol, and polyvinylpyrrolidone;

(b) synthetic polymers of the polyethylene type, e.g. polyethylene and polystyrene;

(c) polymers of the acrylic acid or acrylic acid ester type, e.g. methylmethacrylate or copolymers of acrylic monomers;

(d) biopolymers or modified biopolymers, such as cellulose or cellulose derivatives, e.g. ethylcellulose, cellulose acetate phthalate, cellulose acetate, hydroxypropyl cellulose, hydroxypropylmethyl cellulose, methylcellulose, microcrystalline cellulose, Na-carboxymethyl cellulose, as well as, for example, shellac and gelatin;

(e) fats, oils, higher fatty acids and higher alcohols (i.e. acids and alcohols containing alkyl chains of at least 10 carbon atoms), e.g. aluminum monostearate, cetylalcohol, hydrogenated beef tallow, hydrogenated castor oil, 12-hydroxystearl alcohol, glyceryl mono-or dipalmitate, glyceryl mono-, di- or tristearate, myristyl alcohol, stearic acid, stearyl alcohol, and polyethyleneglycols;

(f) waxes, e.g. bees' wax, camauba wax, Japan wax, paraffin, spernaceti, and synthetic waxes; and (g) sugars and sugar alcohols, e.g. mannitol, sorbitol, sucrose, xylitol, glucose, and maltose.

Depending on the technique used, the polymers mentioned above can be used as coating agents, matrix adjuvants or pharmaceutical binders. Whether the polymer will function as a matrix adjuvant or a pharmaceutical binder will be dependent on the amount of polymer in the formulation.

Combinations of the above mentioned polymers, fats and waxes can also be used for microencapsulation purposes as well as for matrix formation, viz. different polymers can be mixed, a polymer can be mixed with a fat or wax, and so forth.

The encapsulation of the drug can be achieved in the form of microcapsules, but the encapsulation is not restricted to the micro size, i.e. the range of 50 $\mu$m to 2000 $\mu$m.

The multiparticulate dosage forms, i.e., microcapsules or coated pellets as well as the matrix tablets useful for the present invention can be prepared by any of several known production processes, including conventional granulation and tableting of matrix tablets, pan coating, prilling, extrusion and spheronization, fluid bed processes, spray drying, spray chilling, coacervation and other processes.

Microcapsules or Coated Pellets

Microcapsules or coated pellets are defined as a solid or liquid core enclosed in a coating. The coating may also be referred to as the wall or shell. Various types of microcapsule structures can be obtained depending on the manufacturing process, e.g. mononuclear spherical, multinuclear spherical, multinuclear irregular, encapsulated mononuclear capsules, dual-walled microcapsules, etc. Where no distinct coating and core region can be observed, the analogous terms are microparticles, microspheres, micromatrices and microbeads. The microcapsules or pellets of the present invention usually have a particle size between about 1 and about 2000 microns.

The microcapsules or coated pellets of granulated herb can be filled into empty hard gelatin capsules to an extent corresponding to the desired dose, or they can be gently compressed into a tablet by using suitable tablet excipients.;

Coating herbal particles may also be mixed with a pharmaceutical binder to form micropellets, which are then compressed into tablets.

The orally administrable formulations of the invention may comprise micropellets, which are then coated with a pharmaceutically acceptable coating adjuvant prior to being compressed into tablets. The micropellets can also be filled into capsules.

The formulations of the invention may also comprise microspheres which are then coated with a pharmaceutically acceptable coating adjuvant prior to being filled into capsules.

Matrix Formulations

Matrix formulations are defined as a drug or other active ingredient embedded in insoluble excipients in order to achieve release by a continuous leaching of the drug from the inert matrix core. The release mechanisms often follows the square root law of Higuchi. This term also applies to a matrix built of hydrophilic substances which in contact with water form a gel of high viscosity.

One type of matrix formulation is a matrix tablet, which is a matrix formulation in tablet form. Such tablets may be coated with an enteric coating, which inhibits or prevents dissolution of the tablets at low pH (below about pH 5, preferably below about pH 5.5), such as is found in the stomach, and enables dissolution of the tablets at higher pH's (e.g. around pH 6.8, such as is found in the intestine).

EXAMPLES

In one preferred embodiment of the present invention, granulated herb is embedded in hydroxypropyl methyl cellulose and then compressed into a tablet formulation using magnesium stearate as lubricant (round tablet, 6–8 mm in diameter).

In other preferred embodiments of the invention, granulated herb is embedded in a mixture of polyvinyl chloride and ethylcellulose, with the addition of hydroxypropyl methylcellulose, sodium carboxymethyl cellulose or paraffin. The material is then compressed into tablets, using magnesium stearate as lubricant.

In other preferred embodiments of the invention, granulated herb is suspended in a wax melt, e.g. carnauba wax, bees' wax or the like, and then spray chilled into microspheres. The spherical particles can then be coated with a fat or fatty acid, polyethylene glycol or a low melting wax by suspending the microspheres in the low melting excipient and then once again spray chill the slurry into microcapsules.

The invention will be better understood through the following illustrative and non-limitative Examples.

Example 1

Controlled release granulated St. John's Wort extract was prepared by coating dried St. John's Wort granules of average particle size diameter in the range of about 300 to 1000 $\mu$m and which had been dried at room temperature with a semipermeable membrane as follows: First, 2.95 kgs of dried St. John's Wort granules were fluidized in a modified fluid bed coater (GPCG3, Glatt). The inlet temperature was adjusted to achieve a product temperature of 25° C. The granules were then sprayed with a solution made according to the list below:

| Acetone | 1.62 kg |
|---|---|
| Isopropanol | 1.62 kg |
| Methanol | 0.45 kg |
| Klucel | 0.09 kg |
| Ethylcellulose | 0.5 kg |
| Castor oil | 0.036 kg |

The speed of spraying was adjusted in order to obtain a good and homogeneous film on the St. John's Wort granules. The preparation was tested for its slow release properties by dissolution using an USP Apparatus II (paddles as described in USP XXIII) in 900 ml simulated intestinal fluid (without the digestive enzymes normally found in intestinal fluid) containing 0.1% SDS (Sodium Dodecyl Sulfate).

As illustrated in FIG. 1, which illustrates the results of a single trial, the preparation afforded slow release of Hypericin into the medium in comparison to the release of hypericin from raw material. Results of several trials showed that within the first hour, between 25% and 50% of total hypericin was released; in the first two hours, between about 50% and 65% of the total amount of hypericin; in the first four hours between 25% and 70% of the total amount of hypericin and in the first 8 hours more than 75% of the total hypericin were released.

Figure 2:
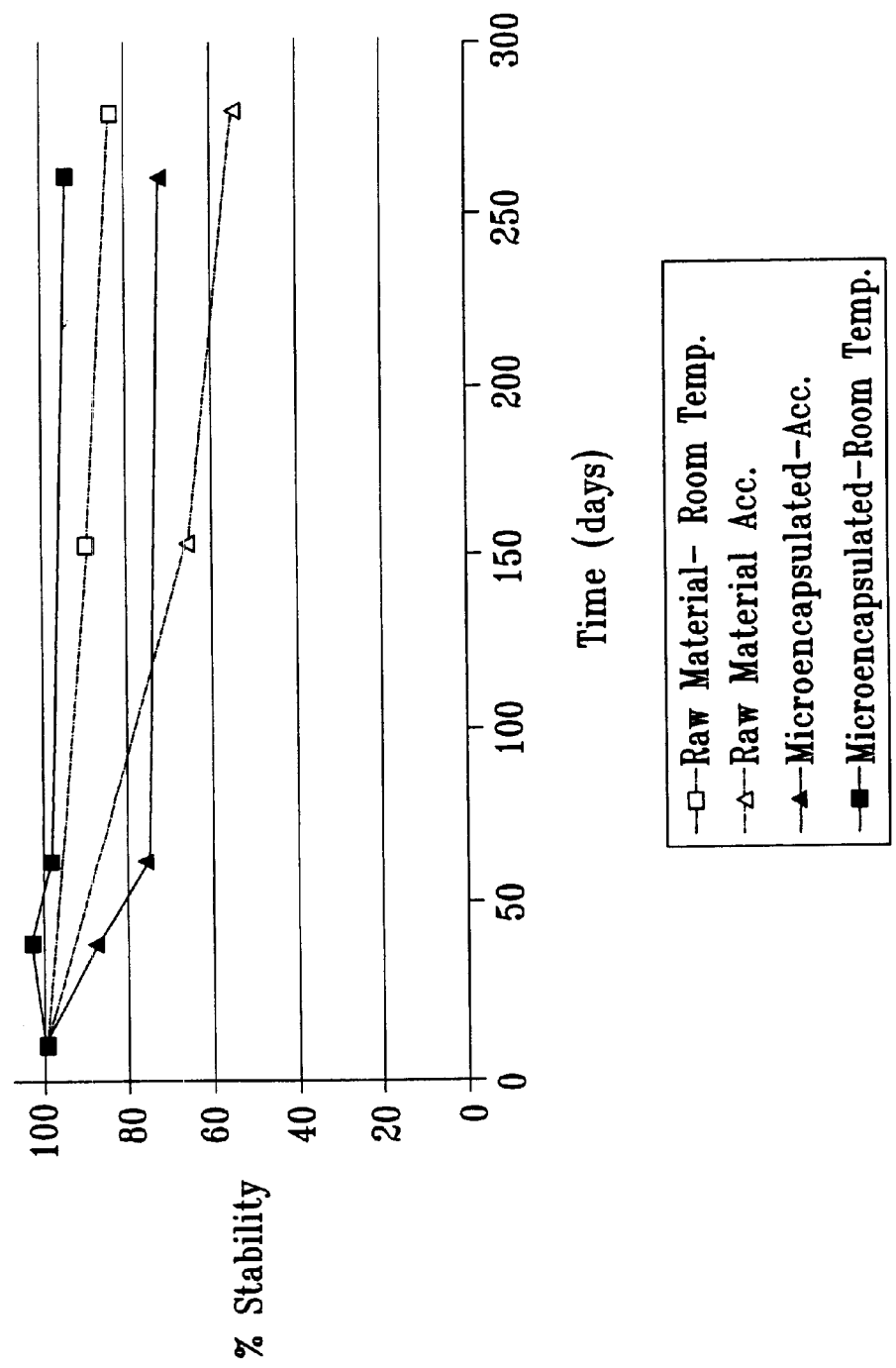

Stability studies were conducted by incubating samples of raw material and mictoencapsulated product in sealed laminated bags under two conditions: at room temperature and ambient (changing) humidity, and at a temperature of 40° C. and 75% humidity. At regular intervals, samples were removed and the degree of decomposition of the active material (hypericin) was determined using HPLC. As shown in FIG. 2, material coated in accordance with the invention showed a significant improvement in stability over non-coated material.

Example 2

Controlled release granulated Ginkgo Biloba extract was prepared by coating dried Gingko Biloba granules, of average particle size diameter in the range of about 300 to 1000 µm and which had been dried at room temperature, with a semipermeable membrane as follows: First, 2.95 kgs of dried Ginkgo Biloba granules were fluidized in a modified fluid bed coater (GPCG3, Glatt). The inlet temperature was adjusted to achieve a product temperature of 20° C. The granules were then sprayed with a solution made according to the list below:

| Acetone | 3.00 kg |
| Isopropanol | 2.40 kg |
| Ethylcellulose | 0.60 kg |
| Castor oil | 0.06 kg |
| Hydroxypropyl methylcellulose | 0.12 kg |
| Methanol | 0.55 kg |

The speed of spraying was adjusted in order to obtain a good and homogeneous film on the Ginkgo Biloba granules. The preparation was tested for its slow release properties by dissolution using an USP Apparatus II (paddles as described in USP XXIII) in 900 ml simulated intestinal fluid (without the digestive enzymes normally found in intestinal fluid) containing 0.1% SDS.

Figure 3:
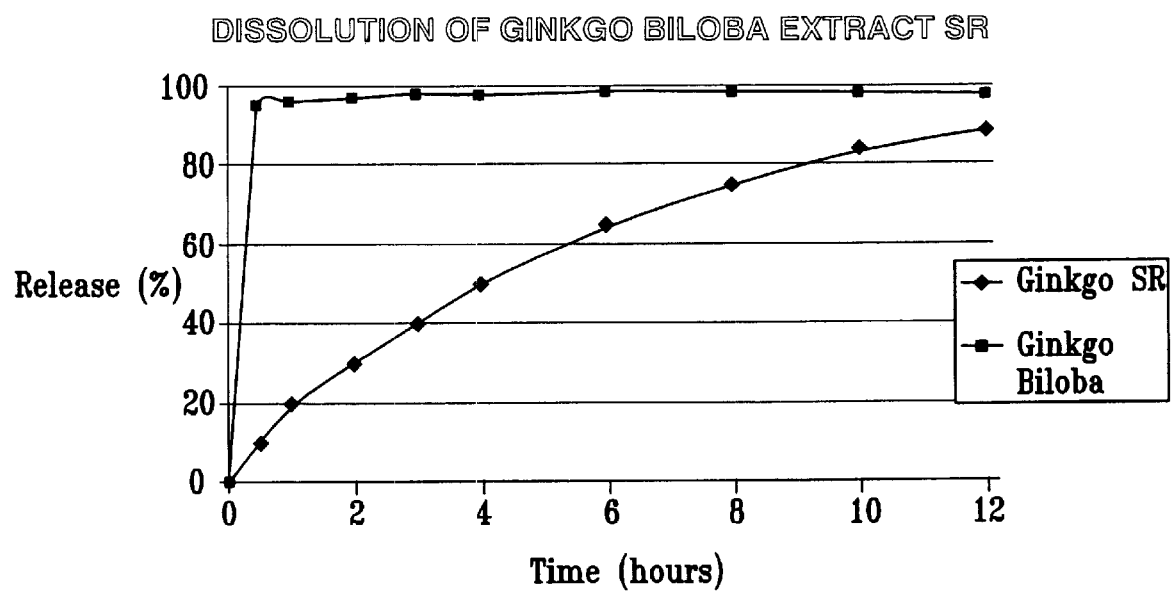

As illustrated in FIG. 3, which shows the result of a single trial, the preparation afforded slow release of the extract ("Ginkgo SR", as measured by ultraviolet (UV) absorption spectroscopy) into the medium. Results of several trials showed that within the first hour, between 10% to 30% of the total extract was released, in the first two hours between about 20% and about 45% of the total amount of extract was released, in the first four hours between about 40% and 60% of the total amount of extract was released and within the first 12 hours more than 75% of the total extract was released.

Figure 4:
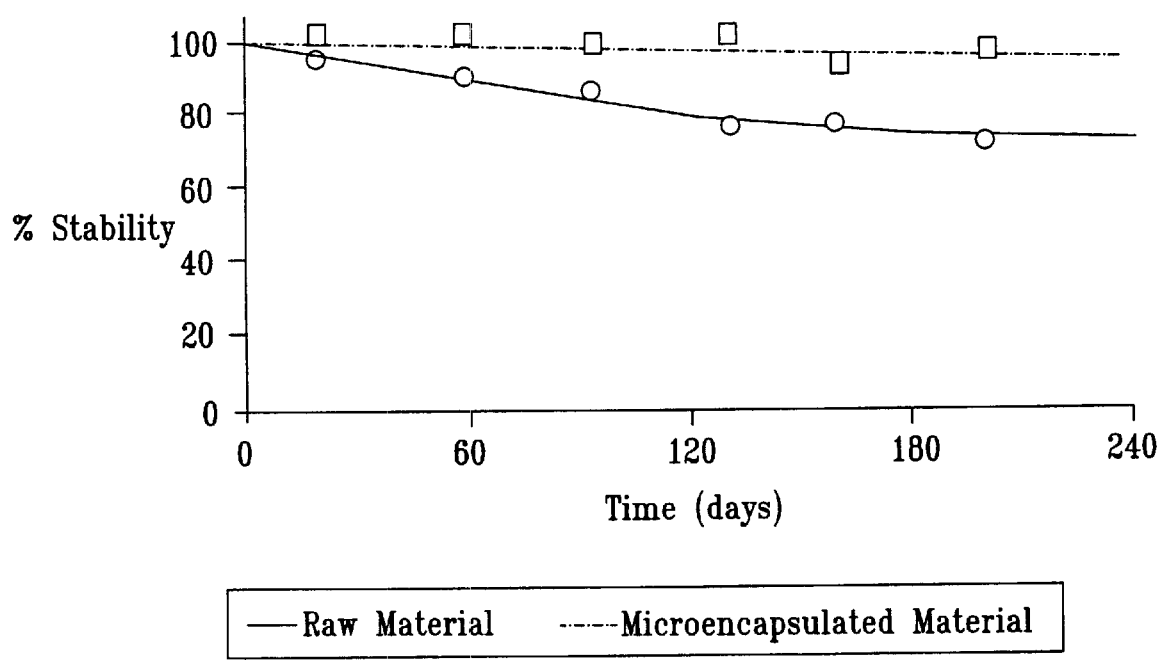

Stability studies were conducted as described in Example 1. As shown in FIG. 4, material coated in accordance with the invention showed a significant improvement in stability over non-coated material.

Example 3

Controlled release granulated Echinacea extract was prepared by coating dried Echinacea granules, of average particle size diameter in the range of about 300 to 1000 µm and which had been dried at room temperature, with a semipermeable membrane as follows: First, 2.95 kgs of dried Echinacea granules were fluidized in a modified fluid bed coater (GPCG3, Glatt). The inlet temperature was adjusted to achieve a product temperature of 20° C. The granules were then sprayed with a solution made according to the list below:

| Acetone | 3.0 kg |
| Isopropanol | 1.8 kg |
| Ethylcellulose | 0.60 kg |
| Methylcellulose | 0.06 kg |
| Castor oil | 0.05 kg |

The speed of spraying was adjusted in order to obtain a good and homogeneous film on the Echinacea granules. The preparation was tested for its slow release properties by dissolution using an USP Apparatus II (paddles as described in USP XXIII) in 900 ml simulated intestinal fluid (without the digestive enzymes normally found in intestinal fluid) containing 0.1% SDS.

Figure 5:
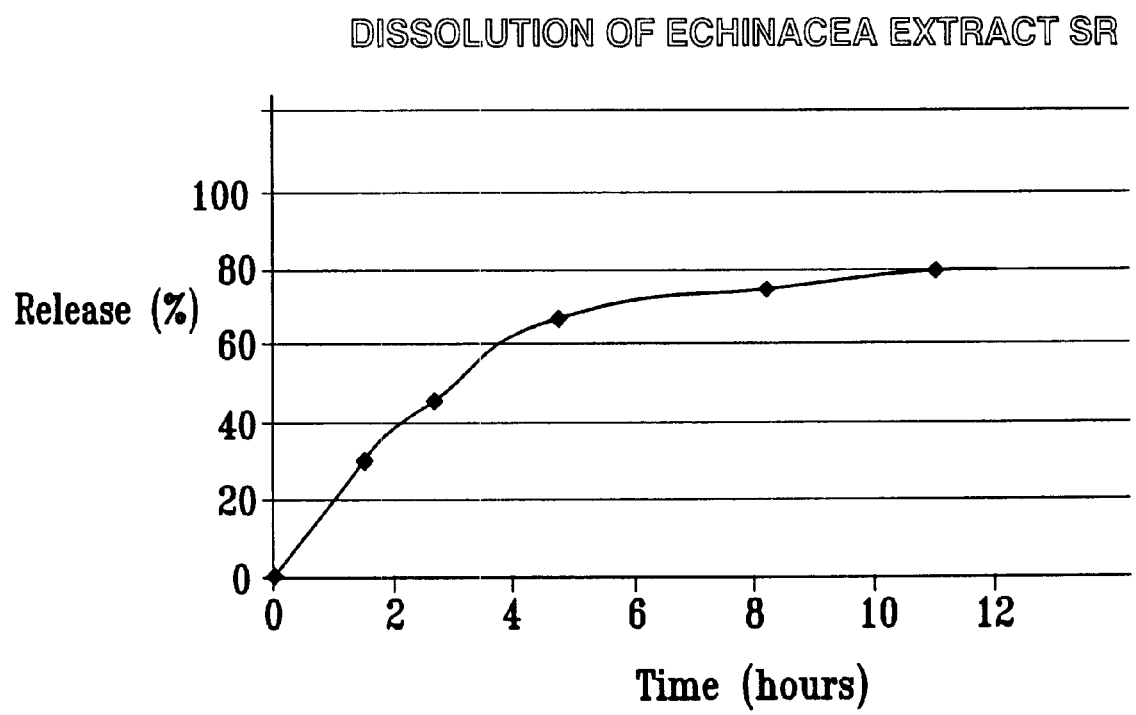

As illustrated in FIG. 5, which shows the result of a single trial, the preparation afforded slow release of the extract into the medium (as measured by UV absorption spectroscopy). Results of several trials showed that within the first hour, between 10% to 30% of the total extract was released, in the first two hours between about 20% and about 40% of the total amount of extract was released, in the first four hours between about 40% and 70% of the total amount of extract was released and within the first 8 hours more than 75% of the total extract was released.

Figure 6:
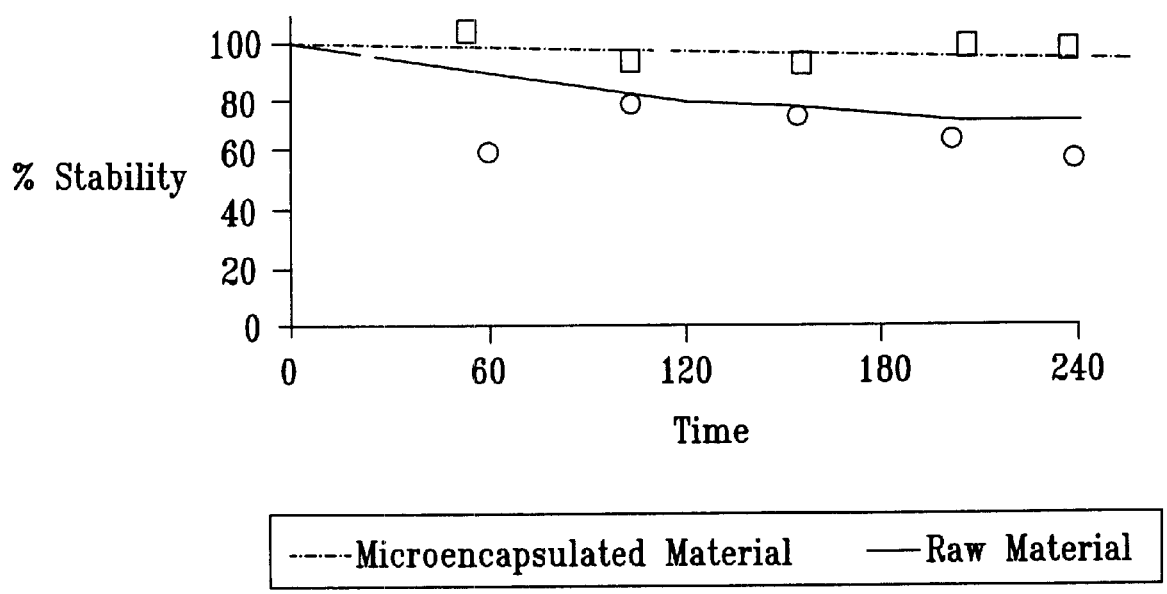

Stability studies were conducted in as in Example 1. As shown in FIG. 6, material coated in accordance with the invention showed a significant improvement in stability over non-coated material.

Example 4

Controlled release granulated Ginseng Root extract was prepared by coating dried Ginseng granules, of average particle size diameter in the range of about 300 to 1000 µm and which had been dried at room temperature, with a semipermeable membrane as follows: First, 2.95 kgs of dried Ginseng granules were fluidized in a modified fluid bed coater (GPCG3, Glatt). The inlet temperature was adjusted to achieve a product temperature of 20° C. The granules were then sprayed with a solution made according to the list below:

| Acetone | 2.0 kg |
| Isopropanol | 1.6 kg |
| Methanol | 0.4 kg |
| Klucel | 0.07 kg |
| Ethylcellulose | 0.42 kg |
| Castor Oil | 0.04 kg |

The speed of spraying was adjusted in order to obtain a good and homogeneous film on the Ginseng granules. The preparation was tested for its slow release properties by dissolution using an USP Apparatus II (paddles as described in USP XXIII) in 900 ml simulated intestinal fluid (without the digestive enzymes normally found in intestinal fluid) containing 0.1% SDS.

Figure 7:
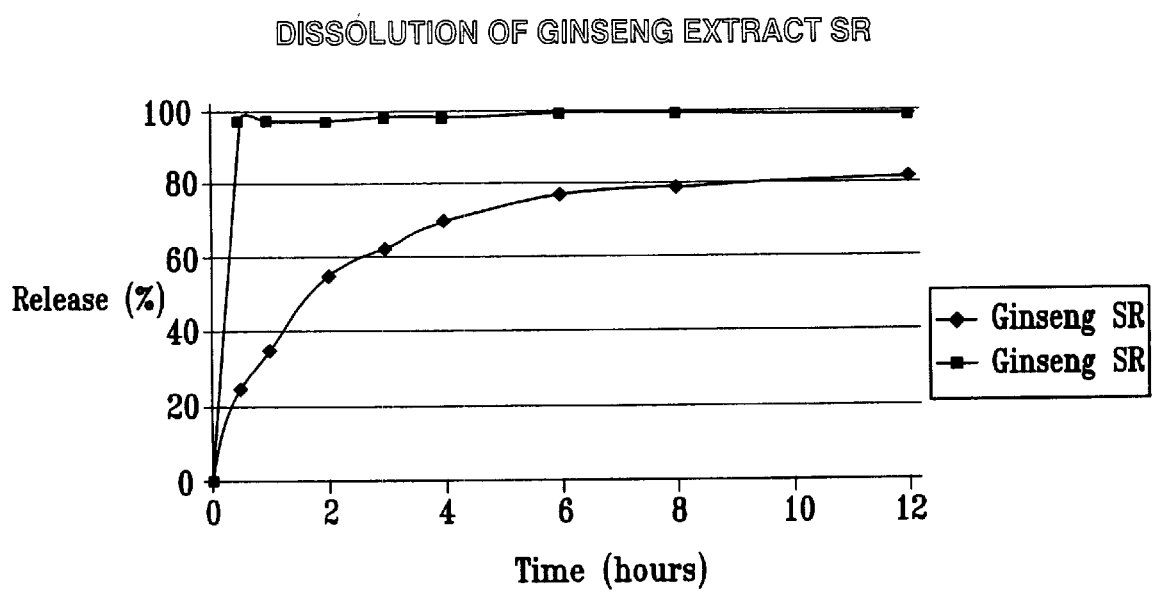

As illustrated in FIG. 7, which shows the result of a single trial, the preparation afforded slow release of ginseng into the medium ("Ginseng SR", as measured by UV absorption spectroscopy). Results of several trials showed that within the first hour, between 25% and 45% of the total ginseng was released, in the first two hours between about 40% and about 65% of the total amount of ginseng was released, in the first four hours between about 50% and 75% of the total amount of extract was released and within the first 8 hours more than 75% of the total amount of ginseng was released.

Figure 8:
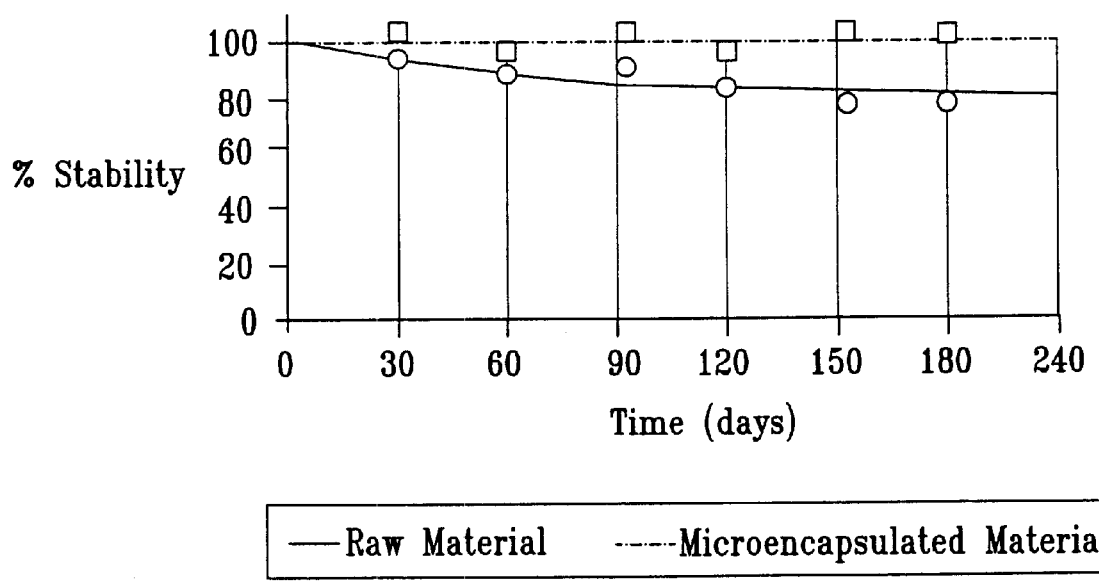

Stability studies were conducted in as in Example 1. As shown in FIG. 8, material coated in accordance with the invention showed a significant improvement in stability over non-coated material.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. An orally-administrable formulation for the controlled release of a granulated herb comprising a microencapsulated granulated herb having an active ingredient selected from the group consisting of hypericin, hyperforine and echinosides and at least one carrier, adjuvant or excipient therefor, characterized in that the total in vitro dissolution time of said formulation required for release of 75% of the active ingredients available from said formulation is between about 4 and about 18 hours, as determined by the U.S.P. XXIII paddle method at a paddle speed of 150 rpm, using simulated intestinal fluid without the digestive enzymes normally found in intestinal fluid, containing 0.1% w/w sodium dodecyl sulfate at pH 6.8 and a temperature of 37° C.

2. formulation according to claim 1 characterized in that it contains from 1 to 95 wt. % granulated herb.

3. A formulation according to claim 1, wherein said formulation is in a form selected from the group consisting of: a matrix tablet, a multicomponent formulation, a microcapsule of generally spherical shape, a microcapsule of generally non-spherical shape, a capsule containing microcapsules, and a table containing microcapsules.

4. A formulation according to claim 1 comprising granulated herb mixed or coated with an adjuvant or mixture of adjuvants selected from the group consisting of synthetic polyvinyl-based polymers, synthetic polyethylene-based polymers, cellulose-based polymers, synthetic polyacrylate-based polymers, fats, waxes, sugars and sugar alcohols.

5. A formulation according to claim 1 in the form of a tablet comprising: granulated herb embedded in a mixture of polyvinyl chloride and polyvinyl acetate; and magnesium stearate as a lubricant.

6. A formulation according to claim 1 in the form of a tablet comprising: granulated herb embedded in a mixture of polyvinyl chloride and ethyl cellulose; magnesium stearate as lubricant; and a material selected from hydroxypropyl methyl cellulose, sodium carboxymethyl cellulose and paraffin.

7. A formulation according to claim 1 in the form of a hard gelatin two-piece capsule filled with microcapsules containing granulated herb.

8. A formulation according to claim 1 in the form of a tablet comprising microcapsules.

9. An orally-administrable formulation for the controlled release of a granulated herb having an active ingredient selected from the group consisting of hypericin, hyperforine and echinosides, comprising microencapsulated particles of a granulated herb having an active ingredient selected from the group consisting of hypericin, hyperforine and echinosides which is coated with an enteric coating comprising a polymer film comprising a polymer which is insoluble at a pH below about 5.5, characterized in that the total in vitro dissolution time of said formulation required for release of 75% of the active ingredients available from said formulation is between about 4 and about 18 hours, as determined by the U.S.P. XXIII paddle method at a paddle speed of 150 rpm, using simulated intestinal fluid without the digestive enzymes normally found in intestinal fluid, containing 0.1% w/w sodium dodecyl sulfate at pH 6.8 and a temperature of 37° C.

10. An orally-administrable formulation according to claim 9, wherein said particles comprise particles which are non-spherically shaped.

11. An orally-administrable formulation according to claim 9, wherein said particles comprise particles which are spherically shaped.

12. A formulation according to claim 9, wherein said polymer is soluble at a pH of about 5.5 or higher.

13. A formulation according to claim 9, wherein said polymer is insoluble at a pH below about 5.0.

14. A formulation according to claim 9, wherein said polymer is hydroxypropylmethyl cellulose phthalate.

15. A formulation according to claim 9, wherein said polymer is cellulose acetate phthalate.

* * * * *